(12) United States Patent
Lindacher et al.

(10) Patent No.: US 8,770,745 B2
(45) Date of Patent: Jul. 8, 2014

(54) LENS HAVING AN OPTICALLY CONTROLLED PERIPHERAL PORTION AND A METHOD FOR DESIGNING AND MANUFACTURING THE LENS

(75) Inventors: Joseph Michael Lindacher, Suwanee, GA (US); Ming Ye, Fort Worth, TX (US)

(73) Assignee: Novartis AG, Basel (CH)

( * ) Notice: Subject to any disclaimer, the term of this patent is extended or adjusted under 35 U.S.C. 154(b) by 230 days.

(21) Appl. No.: 12/906,780

(22) Filed: Oct. 18, 2010

(65) Prior Publication Data

US 2011/0032474 A1    Feb. 10, 2011

Related U.S. Application Data (62) Division of application No. 11/973,458, filed on Oct. 9, 2007.

(60) Provisional application No. 60/828,793, filed on Oct. 10, 2006, provisional application No. 60/829,055, filed on Oct. 11, 2006.

(51) Int. Cl.
*G02C 7/04* (2006.01)
*G02C 7/06* (2006.01)

(52) U.S. Cl.
USPC ............ 351/159.05; 351/159.41; 351/159.79; 623/6.28

(58) Field of Classification Search
USPC .............. 351/159.05, 159.41, 159.78, 159.79
See application file for complete search history.

(56) References Cited

U.S. PATENT DOCUMENTS

| | | | |
|---|---|---|---|
| 4,155,626 A | 5/1979 | Grech | |
| 4,573,775 A | 3/1986 | Bayshore | |
| 4,958,924 A | 9/1990 | Parker | |
| 5,030,231 A | 7/1991 | Portney | |
| 5,121,980 A * | 6/1992 | Cohen | 351/161 |
| 5,408,281 A | 4/1995 | Zhang | |
| 5,652,638 A | 7/1997 | Roffman | |

(Continued)

FOREIGN PATENT DOCUMENTS

| | | |
|---|---|---|
| EP | 0745876 A2 | 12/1996 |
| WO | 9712272 A1 | 4/1997 |

(Continued)

OTHER PUBLICATIONS

International Preliminary Report on Patentability; The International Bureau of WIPO; 34, chemin des Colombettes, 1211 Geneva 20, Switzerland; dated Apr. 15, 2009; 8 pages.

(Continued)

*Primary Examiner* — Jordan Schwartz
(74) *Attorney, Agent, or Firm* — Robert Ambrose (57) ABSTRACT

A contact lens or phakic IOC lens is provided with a peripheral portion that has a power profile that provides optical control of peripheral vision images. Typically, the central portion of the lens is also provided with optical control. The power profile of the lens at the boundary of the central and peripheral portions meets certain boundary conditions that ensure that the lens provides a desired or selected vision correction. Because the peripheral portion of the lens provides optical control that defocuses the peripheral vision image relative to the retina, the lens can be used to prevent or inhibit growth of the eye, thereby preventing or inhibiting myopia or the effects of myopia.

15 Claims, 5 Drawing Sheets

(56) References Cited

U.S. PATENT DOCUMENTS

| | | | |
|---|---|---|---|
| 5,691,797 A | 11/1997 | Seidner | |
| 5,864,379 A | 1/1999 | Dunn | |
| 5,898,473 A | 4/1999 | Seidner | |
| 5,929,969 A | 7/1999 | Roffman | |
| 6,030,077 A | 2/2000 | Sawano | |
| 6,045,578 A | 4/2000 | Collins et al. | |
| 6,176,579 B1 * | 1/2001 | Mandell | 351/159.22 |
| 6,260,966 B1 | 7/2001 | Sawano | |
| 6,286,956 B1 | 9/2001 | Oyama | |
| 6,343,861 B1 | 2/2002 | Kris | |
| 6,364,481 B1 * | 4/2002 | O'Connor et al. | 351/159.05 |
| 6,364,483 B1 * | 4/2002 | Grossinger et al. | 351/161 |
| 6,457,826 B1 * | 10/2002 | Lett | 351/159.05 |
| 6,474,814 B1 | 11/2002 | Griffin | |
| 6,540,353 B1 | 4/2003 | Dunn | |
| 6,695,449 B2 | 2/2004 | Ye | |
| 6,752,499 B2 | 6/2004 | Aller | |
| 6,874,887 B2 | 4/2005 | Tyson | |
| 7,025,460 B2 | 4/2006 | Smitth et al. | |
| 7,036,931 B2 | 5/2006 | Lindacher | |
| 7,040,757 B2 | 5/2006 | Hall | |
| 7,178,918 B2 | 2/2007 | Griffin | |
| 7,287,852 B2 | 10/2007 | Fiala | |
| 7,401,922 B2 | 7/2008 | Legerton | |
| 7,490,937 B2 | 2/2009 | Ye | |
| 7,503,655 B2 | 3/2009 | Smith, III et al. | |
| 7,506,983 B2 | 3/2009 | To | |
| 7,637,612 B2 | 12/2009 | Menezes | |
| 7,665,842 B2 | 2/2010 | Ho et al. | |
| 7,766,478 B2 | 8/2010 | Phillips | |
| 7,766,482 B2 | 8/2010 | Smith, III | |
| 7,803,153 B2 | 9/2010 | Thorn | |
| 7,832,859 B2 | 11/2010 | Phillips | |
| 7,862,171 B2 | 1/2011 | Varnas | |
| 7,909,465 B2 | 3/2011 | Ho | |
| 7,992,997 B2 | 8/2011 | Varnas | |
| 7,997,725 B2 | 8/2011 | Phillips | |
| 7,997,727 B2 | 8/2011 | Ho | |
| 8,192,020 B2 | 6/2012 | Goto | |
| 8,201,941 B2 | 6/2012 | Choo | |
| 8,240,847 B2 | 8/2012 | Holden | |
| 2003/0043342 A1 | 3/2003 | Seidner | |
| 2003/0058404 A1 | 3/2003 | Thorn | |
| 2003/0123024 A1 | 7/2003 | Dunn | |
| 2004/0201821 A1 | 10/2004 | Tyson | |
| 2004/0237971 A1 | 12/2004 | Radhakrishnan | |
| 2005/0041203 A1 | 2/2005 | Lindacher | |
| 2005/0105047 A1 | 5/2005 | Smitth, III | |
| 2006/0015180 A1 | 1/2006 | Peyman et al. | |
| 2006/0082729 A1 | 4/2006 | To | |
| 2006/0176572 A1 * | 8/2006 | Fiala | 359/643 |
| 2007/0115431 A1 | 5/2007 | Smith, III | |
| 2007/0159601 A1 | 7/2007 | Ho | |
| 2007/0258143 A1 * | 11/2007 | Portney | 359/565 |
| 2007/0296916 A1 | 12/2007 | Holden et al. | |
| 2008/0062380 A1 | 3/2008 | Phillips | |
| 2008/0084534 A1 | 4/2008 | Lindacher | |
| 2008/0212022 A1 | 9/2008 | Ye | |
| 2008/0218687 A1 | 9/2008 | Phillips | |
| 2008/0309882 A1 | 12/2008 | Thorn | |
| 2009/0161065 A1 | 6/2009 | Smith, III et al. | |
| 2009/0257026 A1 | 10/2009 | Varnas et al. | |
| 2009/0303442 A1 | 12/2009 | Choo et al. | |
| 2009/0310082 A1 | 12/2009 | Varnas | |
| 2010/0057202 A1 * | 3/2010 | Bogaert | 623/6.27 |
| 2010/0110371 A1 | 5/2010 | Ho | |
| 2010/0225883 A1 | 9/2010 | Ho | |
| 2010/0296050 A1 | 11/2010 | Goto | |
| 2010/0296058 A1 | 11/2010 | Ho | |
| 2011/0001923 A1 | 1/2011 | Phillips | |
| 2011/0037944 A1 | 2/2011 | Varnas | |

FOREIGN PATENT DOCUMENTS

| | | |
|---|---|---|
| WO | WO 01/08605 A1 | 2/2001 |
| WO | 0153878 A1 | 7/2001 |
| WO | 02088831 A1 | 11/2002 |
| WO | 2005055891 A1 | 6/2005 |
| WO | 2006004440 A2 | 1/2006 |
| WO | 2007041796 A1 | 4/2007 |
| WO | 2007075975 A2 | 7/2007 |
| WO | 2007082268 A2 | 7/2007 |
| WO | 2007092853 A2 | 8/2007 |
| WO | 2007146673 A2 | 12/2007 |
| WO | 2008014544 A1 | 2/2008 |
| WO | 2008031166 A1 | 3/2008 |
| WO | 2008045847 A2 | 4/2008 |
| WO | 2008116270 A1 | 10/2008 |
| WO | 2008131479 A1 | 11/2008 |
| WO | 2009129528 A1 | 10/2009 |

OTHER PUBLICATIONS

International Search Report; European Patent Office; P.B. 5818 Patentlaan 2, NL-2280 HV Rijswljk; dated May 2, 2008; 4 pages.

Written Opinion of the International Searching Authority; European Patent Office, D-80298 Munich; dated May 2, 2008; 7 pages.

David R. Williams, et al.; Off-axis Optical Quality and Retinal Sampling in the Human Eye; Vision Res., vol. 36, No. 8, pp. 1103-1114; Printed in Great Britian; 1996; 12 pages.

Authors: David A. Atchison, Catherine E. Jones, Katrina L. Schmid, Nicola Pritchard, James M. Pope, Wendy E. Strugnell, and Robyn A. Riley Title: Eye Shape in Emmetropia and Myopia Published: Investigative Ophthalmology & Visual Science, Oct. 2004, vol. 45, No. 10, pp. 3380-3386 Copyright—Association for Research in Vision and Ophthalmology.

Authors: Krish D. Singh, Nicola S. Logan, and Bernard Gilmartin Title: Three-Dimensional Modeling of the Human Eye Based on Magnetic Resonance Imaging Published: Investigative Ophthalmology & Visual Science, Jun. 2006, vol. 47, No. 6, pp. 2272-2279 Copyright—Association for Reasearch in Vision and Ophthalmology.

Authors: Donald O. Mutti, Robert I. Sholtz, Nina E. Friedman, and Karla Zadnik Title: Peripheral Refraction and Ocular Shape in Children Published: Investigative Ophthalmology & Visual Science, Apr. 2000, vol. 41, No. 5, pp. 1022-1030 Copyright—Association for Research in Vision and Ophthalmology.

\* cited by examiner

LENS HAVING AN OPTICALLY CONTROLLED PERIPHERAL PORTION AND A METHOD FOR DESIGNING AND MANUFACTURING THE LENS

CROSS-REFERENCE TO RELATED APPLICATIONS

This application is a divisional of U.S. Non-Provisional patent application Ser. No. 11/973,458 filed Oct. 9, 2007, which claims the benefits under 35 USC 119(e) of U.S. Provisional Patent Application Nos. 60/828,793 filed Oct. 10, 2006 and 60/829,055 filed Oct. 11, 2006, herein incorporated by reference in their entireties.

TECHNICAL FIELD OF THE INVENTION

The invention relates to contact lenses and phakic intraocular (IOC) lenses used to provide vision correction. More particularly, the invention relates to providing contact lenses and phakic IOC lenses with peripheral portions that are optically controlled.

BACKGROUND OF THE INVENTION

A contact lens is a thin plastic or glass lens that is fitted over the cornea of the eye to correct vision defects. Various types of contact lenses exist that are designed to treat various types of vision defects. A phakic IOC lens is a lens that is implanted behind a person's cornea and works in conjunction with the natural crystalline lens of the eye to provide vision correction. Phakic IOC lenses are typically made of a material called polymethylmethacrylate (PMMA). The term "phakic" means that the eye with which the phakic IOC lens is used possesses the natural crystalline lens of the eye.

Typical lenses, including both contact lenses and phakic IOC lenses, are designed and manufactured to provide only the central portion of the lens with optical control. The central portion of the lens is deemed most important because it affects central vision, which is much more accurate than peripheral vision. The "central portion" of the lens, as that term is used herein, is intended to denote the portion of the lens that is optically controlled to provide an intended optical effect on a person's central vision. The central portion of a typical soft contact lens extends from the center of the lens outwardly to a distance of approximately 3.5 to 4 millimeters (mm) at the periphery of the central portion. This corresponds to a radial distance, r, that ranges from r=0.0 mm at the center of the lens to r≈3.5 or 4.0 mm at the boundary where the central and peripheral portions of the lens meet. The peripheral portion of a typical contact lens has a peripheral portion that starts where the central portion ends (e.g., at r≈3.5 or 4.0 mm) and extends outwardly a radial distance from the lens center of r≈7.0. Thus, the typical soft contact lens has a total diameter of approximately 14.0 mm.

It is believed that central vision is more accurate than peripheral vision due to the relatively high density of photoreceptors in and around the center of the retina of the eye. These photoreceptors, also known as "cones", are responsible for daylight and color vision and are concentrated in a small depression near the center of the retina known as the fovea centralis. This dense concentration of cones provides this region of the retina with the greatest visual acuity. Acuity drops dramatically in the peripheral region of the retina. Central vision allows a person to distinguish smaller features that are near or at the center of the field of view, whereas features that are outside of the center of the field of view must be larger for the person to distinguish them through peripheral vision.

Soft contact lenses are not designed to provide optical control over the peripheral portions of the lenses because the peripheral portions do not affect the central vision of the eye. The light rays that pass through the peripheral portion of a typical soft contact lens are not focused in the central region of the retina, and thus do not affect the central vision of the eye. The peripheral portion of a typical soft contact lens sometimes includes a blending or transitioning portion that connects the central portion to the peripheral portion. This blending portion does not designed to provide optical control, and therefore does not provide vision correction except in cases where the pupils of the eye are small. The purpose of the blending portion is simply to connect the central and peripheral portions to each other.

Although an eye's corneal diameter typically ranges from about 11 mm to about 12 mm, the central portion of a typical soft contact lens typically ranges from about 7 mm to about 8 mm in diameter (i.e., r≈3.5 to 4 mm). The diameter of the central vision zone of the eye is generally defined as the region that provides central vision when the pupil is no larger than 7 mm in diameter under scotopic viewing conditions. The term "scotopic" means the ability to see in darkness or dim light, also referred to as dark-adapted vision. Although a typical soft contact lens is about 14 mm in total diameter, only the central 7 or 8 mm diameter portion provides vision correction. The peripheral portion, also commonly referred to as the lenticular portion, serves to stabilize the lens and fit the lens comfortably over the limbus of the eye.

While the peripheral portion of a typical soft contact lens is not designed to provide optical control over light entering the eye, it has been suggested that peripheral vision images may have important effects on the vision system of the eye. For example, it has been suggested that vision in the peripheral range drives myopia. Myopia is the medical term for nearsightedness. People with myopia see objects that are closer to the eye more clearly, while distant objects appear blurred or fuzzy.

The manner in which peripheral vision may affect the vision system of the eye is explained in, for example, U.S. Pat. No. 7,025,460 to Smith, et al. Specifically, in Column 3, lines 42-47 of Smith et al. states:

"The present invention is based on new learning from our experiments that demonstrates that the peripheral retinal image (i.e. peripheral vision) plays a major role in determining overall eye length, and is an effective stimulus that promotes peripheral and total eye growth that results in axial elongation, an overall increase in eye size and myopia."

Smith et al. discloses various methods and devices for providing a visual image that has "a peripheral field image location that is positioned more anteriorly to (or in front of) the peripheral retina (i.e. toward the cornea or the front of the eye) than normally in the uncorrected condition, while the central field image location is positioned near the central retina (i.e. the fovea)". Smith et al. discloses that this arrangement minimizes or eliminates the stimulus for eye axial elongation leading to myopia.

U.S. Pat. No. 6,045,578 to Collins et al. discloses a method for treating myopia that uses a lens having a central portion (i.e., an optic zone) that causes paraxial light rays entering the center region of the central portion of the lens to be focused on the retina while causing light rays entering the peripheral region of the central portion of the lens to be focused in a plane between the cornea and the retina, thereby producing positive spherical aberration of the image on the retina. Collins et al. states that this positive spherical aberration has a physiological effect on the eye that tends to inhibit growth of the eye, thus mitigating the tendency of the myopic eye to grow longer.

Collins et al. also discloses an embodiment for mitigating hyperopia by using a lens having a central portion (i.e., an optic zone) that causes paraxial light rays entering the center region of the central portion of the lens to be focused on the retina while causing light rays entering the peripheral region of the central portion of the lens to be focused in a plane behind the retina, thereby producing negative spherical aberration of the image on the retina. Collins et al. states that this negative spherical aberration has a physiological effect on the eye that tends to enhance growth of the eye, thus mitigating hyperopia.

While Smith et al. and Collins et al. both recognize the importance of the peripheral vision image, these patents are directed to the effects that light rays passing through the periphery of the central portion of the lens have on the vision system of the eye. In other words, these patents are not directed to the effects that light rays passing through the peripheral portion of the lens (i.e., the portion outside the approximately 7 or 8 mm diameter central portion of the lens) have on the eye. Therefore, the effects that these light rays produce on the vision system are limited by the ability of the central portion of the lens to provide the necessary optical control.

For a variety of reasons, including those described in Smith et al. and Collins et al., it would be desirable to provide a lens having a peripheral portion that provides optical control. However, because the peripheral portion of the lens is used to stabilize the lens and to fit the lens to the surface of the eyeball, and is normally the same for every lens of a given lens series, the peripheral portion is normally not designed to provide optical control. If the peripheral portion were to be designed to provide optical control, it could not be kept the same for an entire lens series. Rather, the peripheral portion would need to be varied from lens to lens in order to ensure that the optical control it provides works with the optical control provided by the central portion. Consequently, the traditional view in the soft contact lens industry is that because central vision is most important, and because providing the peripheral portion of the lens with optical control would require that different lenses of the same series be manufactured with different peripheral portions, it is undesirable to design contact lenses to have peripheral portions that provide optical control.

Furthermore, increasing the diameter of the optical zone of a contact lens presents certain problems that would need to be solved by the contact lens industry. For example, for a typical lens series comprising lenses ranging in optical power from −10 D to +6 D and having 8 mm diameter central portions, the sagittal depth (SAG) difference for different lenses of the series is roughly 20 micrometers (μm) per Diopter. Therefore, both the thickness of the lens at the center of the central portion and at the edge of the central portion vary over a lens series. If the diameter of the central portion were to be increased, the SAG difference across the series would increase to an even greater extent. Because the front surface of the peripheral portion is generally constant across the power range of the series, increasing the diameter of the central portion would require that the slope and curvature of the blending portion be varied to an even greater extent from lens to lens across a given series. This presents even greater difficulties in terms of lens design and manufacture.

Accordingly, a need exists for a contact lens having a peripheral portion that provides optical control and that can be easily designed and manufactured.

SUMMARY OF THE INVENTION

In accordance with the invention, a lens is provided that has a peripheral portion that provides optical control. The peripheral portion of the lens has a power profile that optical controls a location at which a peripheral vision image is focused relative to a retina of an eye. The lens also has a central portion having at least one optical zone that provides optical control over light rays passing through the central portion. The central portion has a power profile that optically controls a location at which a center vision image is focused relative to the retina of the eye.

The invention also provides a method for providing a lens that prevents or inhibits eye growth that leads to myopia. The method comprises selecting a power profile for a peripheral portion of a lens to be designed, and producing a design of a lens that has a peripheral portion that provides optical control based on the selected power profile. The power profile of the peripheral portion optically controls a location at which a peripheral vision image is focused relative to a retina of an eye. The lens design also includes a central portion having a power profile that optically controls a location at which a center vision image is focused relative to the retina of the eye.

These and other features and advantages of the invention will become apparent from the following description, drawings and claims.

DETAILED DESCRIPTION OF ILLUSTRATIVE EMBODIMENTS

In accordance with the invention, the peripheral portion of a contact lens or phakic IOC lens is provided with optical control by controlling the power profile of the peripheral portion of the lens. Typically, the central portion of the lens is also provided with optical control, but because the invention is directed primarily to the peripheral portion of the lens, the invention is not limited with respect to the power profile of the central portion of the lens. The power profile of the lens of the invention at the boundary of the central and peripheral portions meets certain boundary conditions necessary to ensure that the lens provides a desired or selected vision correction, as will be described below in detail with reference to FIGS. 3 and 4.

Figure 1:
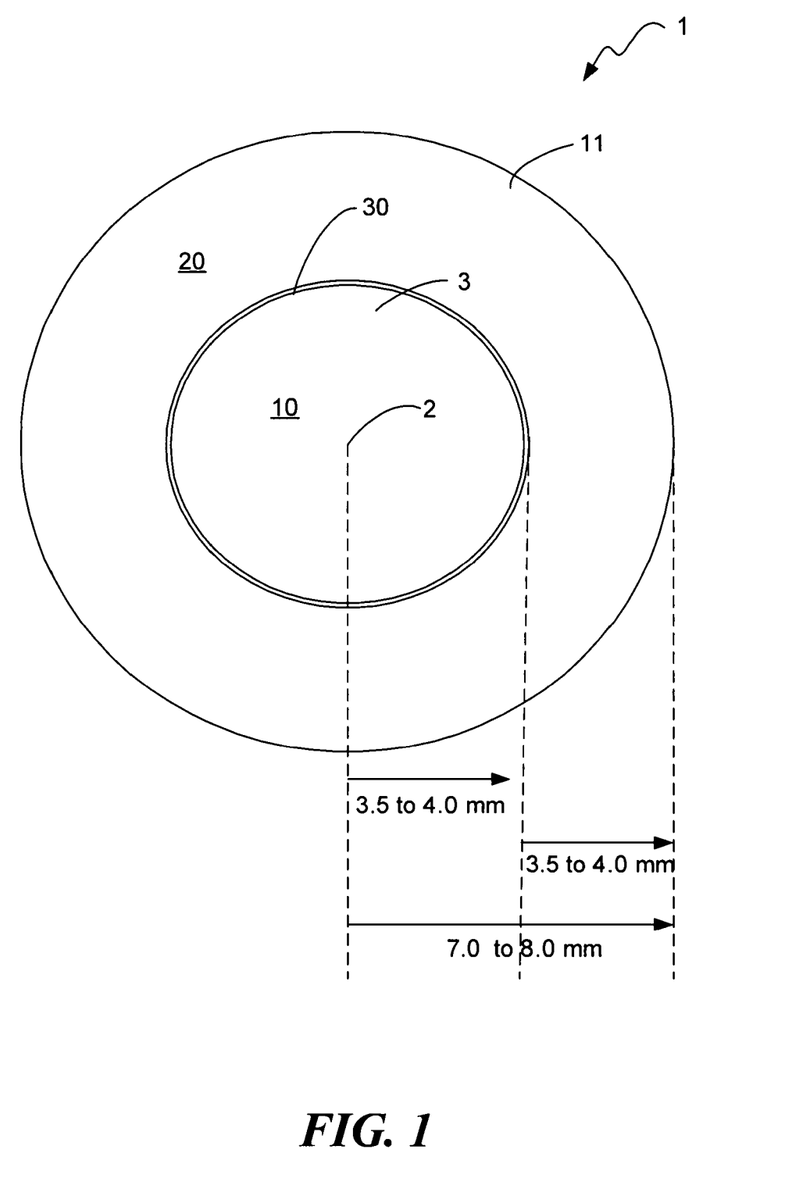
FIG. 1 illustrates a plan view of a lens in accordance with an illustrative embodiment of the invention having a central portion and a peripheral portion, wherein the peripheral portion is optically controlled.

FIG. 1 illustrates a plan view of a contact lens 1 in accordance with an embodiment of the invention. The lens 1 comprises a central portion 10 and a peripheral portion 20. The peripheral portion 20 includes a blending portion 30 that interconnects the central portion 10 and the peripheral portion 20. The central portion 10 has a radius, r, that typically ranges from 0.0 mm at the center 2 of the lens 1 to about 3.5 or 4.0 mm at the outer edge of the periphery 3 of the central portion 10. The peripheral portion 20 has an inner radius, rI, that coincides with the radius, r, of the central portion 10, and an outer radius, rO, that coincides with the outer edge of the periphery 11 of the peripheral portion 20 and is typically about 7.0 mm to about 8.0 mm.

Figure 2:
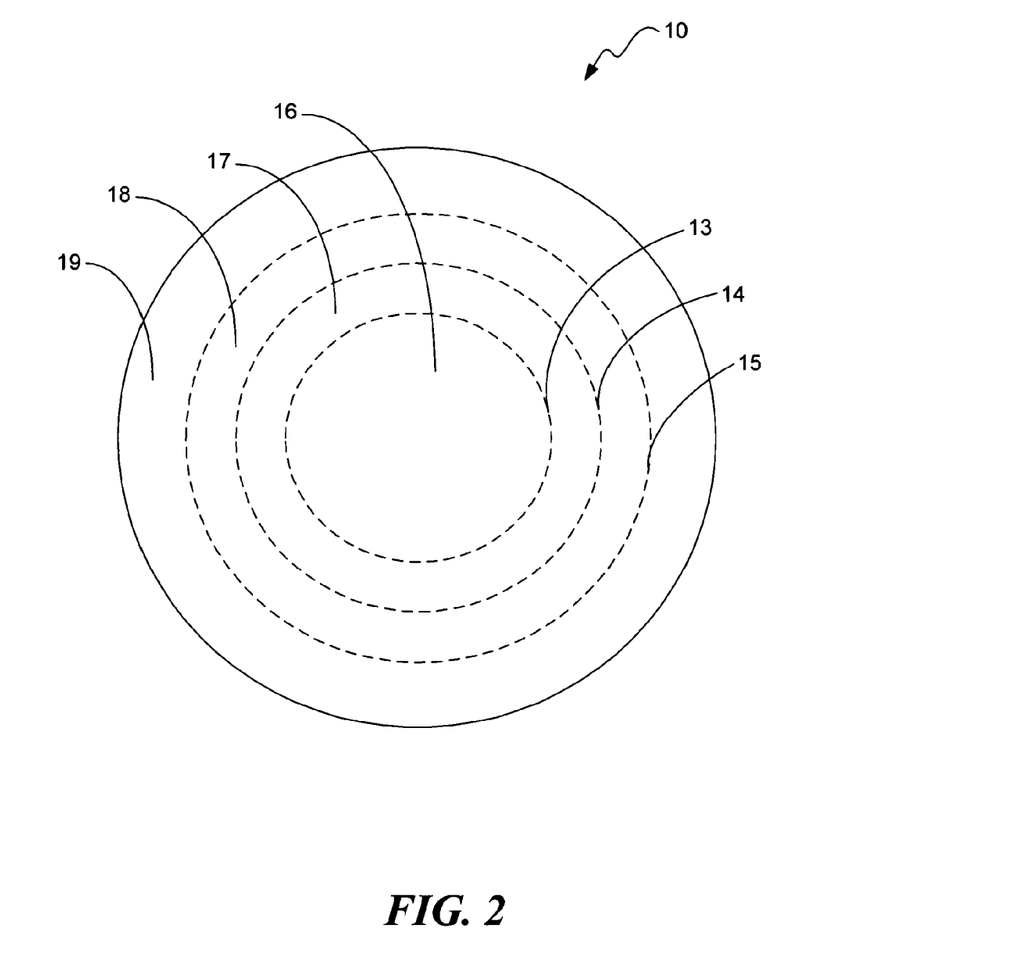
FIG. 2 illustrates a plan view of the central portion of the lens shown in FIG. 1 in accordance with an embodiment having one or more optical zones that are optically controlled.

FIG. 2 illustrates a plan view of the central portion 10 of the lens 1 without the surrounding peripheral portion 20. The central portion 10 of the lens 1 may be made up of a single optical zone or a plurality of optical zones. The invention is not limited with respect to the number of optical zones that make up the central portion 10. The dashed circles 13, 14 and 15 are intended to demark optional optical zones 16, 17, 18 and 19 that make up the central portion. Although the dashed circles 13, 14 and 15 may appear to indicate discrete boundaries between the optical zones, any optical zones making up the central portion 10 will typically be provided with smooth transition regions so that there are not abrupt changes in optical power when transitioning from one zone to another. However, the invention is not limited with regard to the optical zone or zones provided by the central portion 10 or with respect to the optical control provided by the central portion 10.

In one embodiment of the present invention, the power profile that describes the optical control provided by the central portion 10 and by the peripheral portion 20 of the lens 1 is any power profile that is continuous in the first derivative across the boundary (i.e., the blending portion 30) where the central portion 10 and the peripheral portion 20 meet. A large number of mathematical functions exist that satisfy this boundary condition and that are suitable for defining the power profile of the lens 1.

Figure 3:
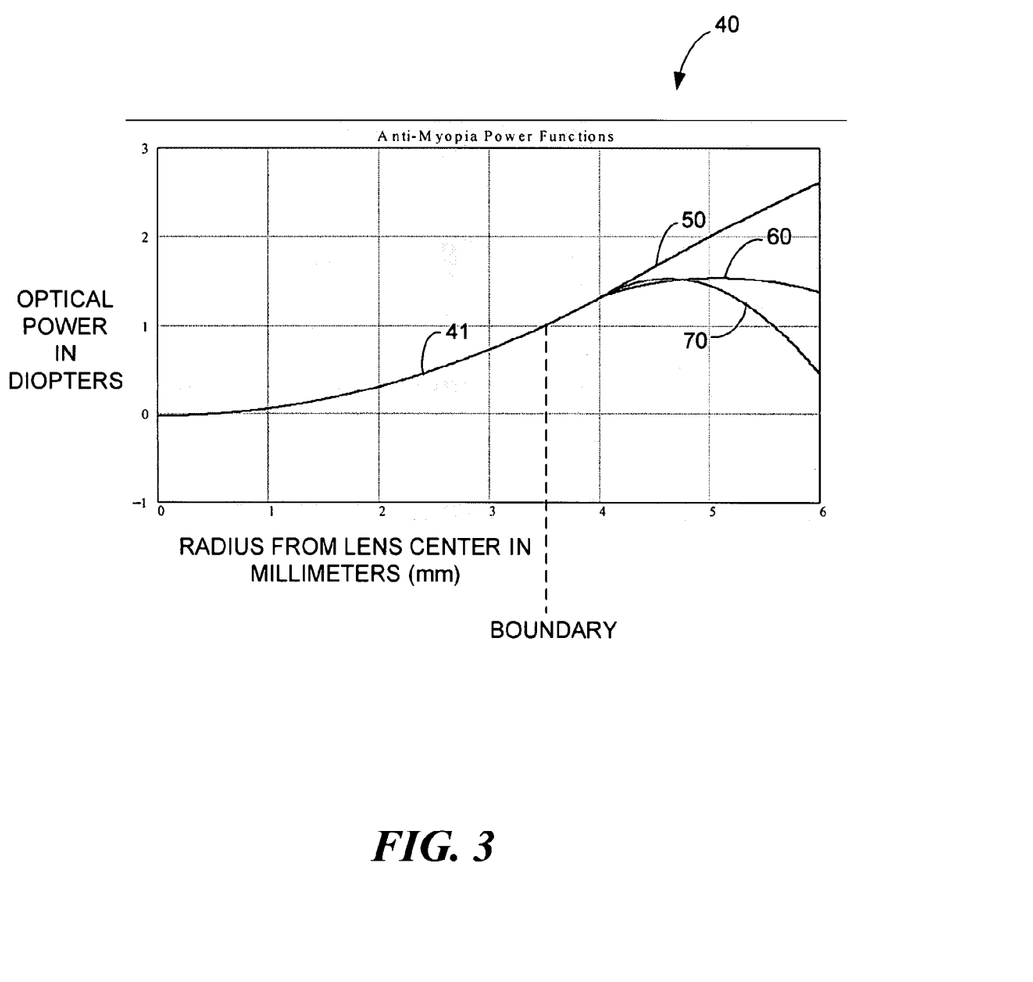
FIG. 3 illustrates a plot that contains three different power profiles that are suitable power profiles for the lens shown in FIG. 1, and which all provide the peripheral portion of the lens with optical control.

FIG. 3 illustrates a plot 40 of three different power profiles 50, 60 and 70 that are suitable power profiles for the lens 1 shown in FIG. 1. The vertical axis of the plot 40 represents optical power in Diopters and the horizontal axis represents the radial distance from the center 2 of the lens 1 outward toward the periphery 11 of the peripheral portion 20 of the lens 1. In this example, the outer periphery 11 of the peripheral portion 20 is a radial distance of approximately 7 mm from the center 2 of the lens 1, but the plot 40 stops at r=6.0 mm because the profile beyond this region is not important in this embodiment. In accordance with this embodiment, the boundary between the central portion 10 and the peripheral portion 20 is a radial distance of approximately 3.5 mm from the center 2 of the lens 1.

Each of the power profiles 50, 60 and 70 is defined by a mathematical function that is differentiable in the first derivative at least at the boundary where the central portion 10 and the peripheral portion 20 meet. In other words, the mathematical functions are continuous at least at the boundary where the central portion 10 and the peripheral portion 20 meet. This means that the first derivative of each of the functions can be taken at least at the boundary. In addition to being differentiable in the first derivative at the boundary where the central portion 10 and the peripheral portion 20 meet, these functions may be, but need not be, differentiable in the second, third and higher order derivatives at the boundary. Therefore, the functions may be higher order functions such as polynomials, for example. Other functions, such as, for example, linear functions and continuous spline functions (e.g., cubic splines and bicubic splines), may also be used to describe the power profiles. Linear functions and cubic and bicubic spline functions are all differentiable in at least the first derivative.

In the central portion 10, the power profiles 50, 60 and 70 are identical and are represented by the portion of the power profile labeled with reference numeral 41. This portion of the power profile corresponds to the typical Seidel, Zernike, conic and biconic mathematical functions commonly used to define power profiles for soft contact lenses prescribed for treating myopia and hyperopia. The invention is not limited to the power profiles 50, 60 and 70 shown in FIG. 3, and is not limited with respect to the power profile in the central portion 10 of the lens 1. The power profiles shown in FIG. 3 are merely examples of power profiles that are continuous in the first derivative and that are suitable power profiles for the lens 1 shown in FIG. 1.

For most uncorrected eyes, the peripheral vision image is formed behind the retina. Each of the power profiles 50, 60 and 70 has an ADD power in the peripheral portion 20 that is greater than zero. Consequently, each of the power profiles 50, 60 and 70 will provide a positive ADD power that will pull the peripheral vision image in a direction toward the cornea from either behind the retina, on the retina or in front of the retina. The power profile selected for the peripheral portion will depend on the patient and the amount of vision correction needed or desired. For example, in some cases, the patient may have an uncorrected vision that results in the peripheral vision image being focused behind the retina. In this case, fitting the patient with a lens that has the profile 50 will provide a relatively large ADD power that will move the peripheral vision image so that it is focused in front of the retina.

If the patient has an uncorrected vision that results in the peripheral vision image being focused on the retina, fitting the patient with a lens that has the profile 60 will provide a lower ADD power that will move the peripheral vision image from being focused on the retina to being focused in front of the retina. Similarly, if the patient has an uncorrected vision that results in the peripheral vision image being focused slightly in front of the retina, fitting the patient with a lens that has the profile 70 will provide a small ADD power that will move the peripheral vision image a little more in the direction toward the cornea.

In all of these cases, the additional ADD power provided by the lens results in myopic defocus in the peripheral region of the retina. This myopic defocus helps prevent or inhibit eye growth, thereby preventing or inhibiting myopia and/or ameliorating the effects of myopia.

Figure 4:
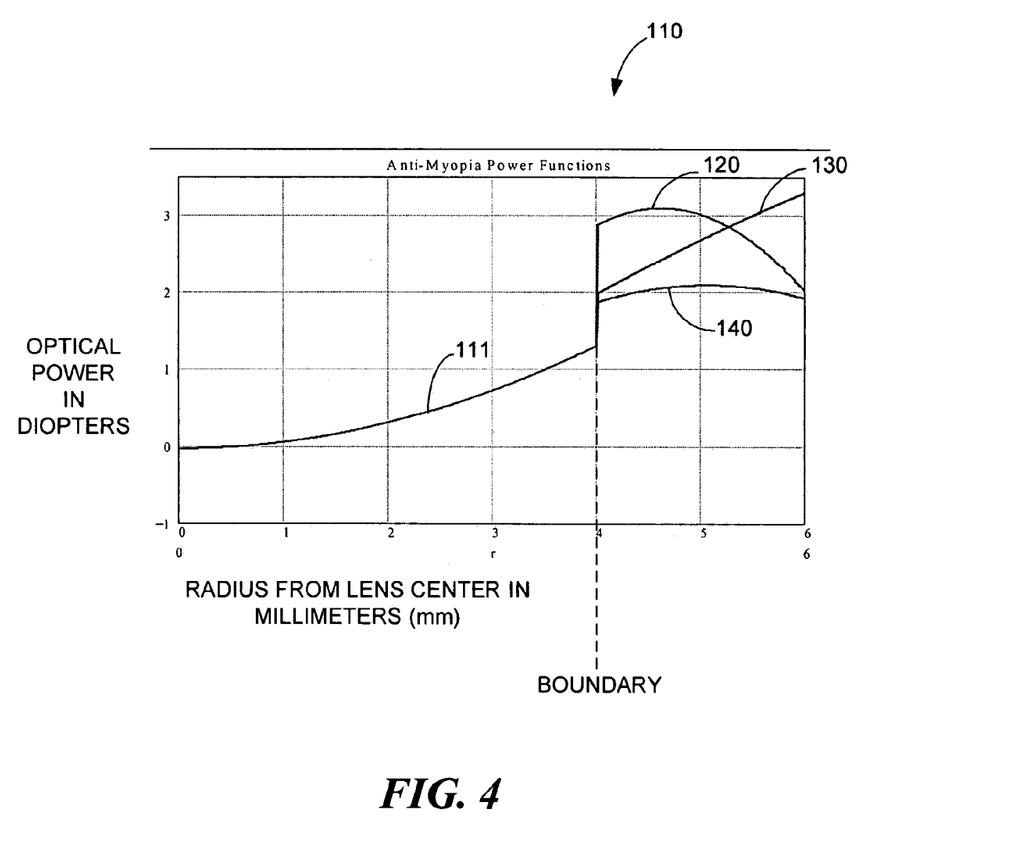
FIG. 4 illustrates a plot that contains three different power profiles that are suitable power profiles for the lens shown in FIG. 1, and which all provide the peripheral portion of the lens with optical control.

FIG. 4 illustrates a plot 110 that contains three different power profiles 120, 130 and 140 that are suitable power profiles for the lens 1 shown in FIG. 1. The power profiles 120, 130 and 140 are, in this example, mathematically identical in the central portion 10, as indicated by portion 111 of the power profile, which extends from the center 2 out to approximately 4.0 mm at the boundary where the central and peripheral portions 10 and 20 meet. In accordance with this embodiment, the power profiles 120, 130 and 140 may or may not be continuous over the boundary between the central and peripheral portions 10 and 20. In other words, at the boundary, the first derivative may not be able to be taken for any of the mathematical functions that describe the profiles 120, 130 and 140.

For example, if the power profile is mathematically defined by a piecewise function, the profile will typically not be continuous at the boundary, and therefore, will not be differentiable in the first derivative at the boundary. In contrast, if the power profile is mathematically defined by a spline function, the profile will typically be continuous at the boundary, but will not be differentiable in the first derivative at the boundary However, provided other boundary conditions are met, a lens having any one of the profiles 120, 130 and 140 will work for its intended purpose regardless of whether it is continuous or discontinuous at the boundary and regardless of whether it is differentiable in the first derivative at the boundary.

In particular, the only boundary condition that needs to be met is that the difference between the optical power in the central portion 10 at the boundary and the optical power in the peripheral portion 20 at the boundary cannot be too great. Provided this boundary condition is met, the lens peripheral portion 20 will provide a positive ADD power that will pull the peripheral vision image in a direction toward the cornea from either behind the retina, on the retina or in front of the retina, depending on the patient's uncorrected vision. Also, the discontinuity in the profiles 120, 130 and 140 at the boundary will not result in artifacts or other undesired effects on the vision system as long as the boundary condition is met.

The difference in optical power in the central portion 10 at the boundary and the optical power in the peripheral portion 20 at the boundary should not be greater than about 8.0 Diopters, and preferably is no greater than about 3.0 Diopters. In the plot 110 shown in FIG. 1, for profile 120, the difference in optical power in the central portion 10 at the boundary and the optical power in the peripheral portion 20 at the boundary is only about 1.6 Diopters, which easily meets the boundary condition. For profile 130, the difference in optical power in the central portion 10 at the boundary and the optical power in the peripheral portion 20 at the boundary is only about 0.7 Diopters, which easily meets the boundary condition. Similarly, for profile 140, the difference in optical power in the central portion 10 at the boundary and the optical power in the peripheral portion 20 at the boundary is only about 0.6 Diopters, which easily meets the boundary condition.

The power profile selected for the peripheral portion 20 will depend on the patient and the amount of vision correction needed or desired. For example, if the patient has an uncorrected vision that results in the peripheral vision image being focused behind the retina, fitting the patient with a lens that has the profile 120 will provide a relatively large ADD power that will move the peripheral vision image so that it is focused in front of the retina. If the patient has an uncorrected vision that results in the peripheral vision image being focused on the retina, fitting the patient with a lens that has the profile 130 will also provide a relatively ADD power that will move the peripheral vision image from being focused on the retina to being focused well in front of the retina. Similarly, if the patient has an uncorrected vision that results in the peripheral vision image being focused slightly in front of the retina, fitting the patient with a lens that has the profile 140 will provide a small ADD power that will move the peripheral vision image a little more in the direction toward the cornea.

In all of these cases, the additional ADD power provided by the lens having the profiles shown in FIG. 4 results in myopic defocus in the peripheral region of the retina. This myopic defocus helps prevent or inhibit eye growth, thereby preventing or inhibiting myopia and/or ameliorating the effects of myopia.

The profiles 120, 130 and 140 may be described by any type of mathematical functions that meet the boundary condition described above, including, for example, spline functions and piecewise functions. The invention is not limited with respect to the mathematical functions that are used to define the profiles in the peripheral portions 20. It should be noted that although the profiles may be discontinuous at the boundary (i.e., not differentiable in the first derivative), the actual lens surfaces preferably are continuous. The manner in which lenses having profiles that are discontinuous at the boundary can be designed and manufactured with continuous surfaces is known in the art. For example, contact lenses having optical zones in the central portions that are defined by splines or piecewise functions are known.

Likewise, the manner in which lenses having profiles that are continuous at the boundary can be designed and manufactured with continuous surfaces is known in the art. For example, contact lenses having optical zones in the central portions that are defined by polynomials are well known.

The optical zone provided by the peripheral portion 20 may be formed on the front surface of the lens or on anterior surface of the lens. The manner in which lenses can be designed and manufactured to meet all of these criteria is also known. Therefore, in the interest of brevity, design and manufacturing techniques that are suitable for use with the present invention will not be described herein.

Figure 5:
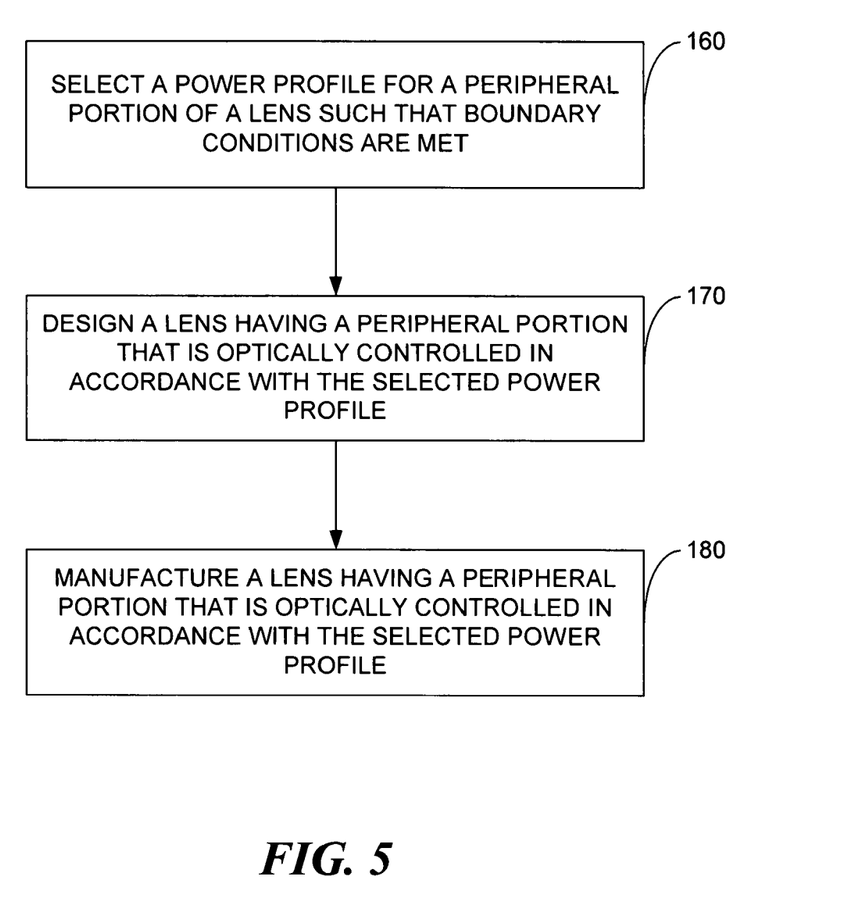
FIG. 5 illustrates a flowchart that represents the method of the invention in accordance with an embodiment.

FIG. 5 illustrates a flowchart that represents the method of the invention in accordance with an embodiment. A selection process is first performed during which a power profile for the peripheral portion of the lens is selected, as indicated by block 160. The selected power profile may be for a single lens or for a lens series. Each lens of a given lens series will have the same power profile.

Once the power profile has been selected, a lens is designed to have a peripheral portion that provides the optical control provided by the selected power profile, as indicated by block 170. During the design process, typically a software program executed by a processor performs receives input from a designer and generates a lens model having the surfaces that define the lens and the selected power profile.

After the lens has been designed, the lens or the corresponding series of lens are manufactured, as indicated by block 180. A variety of manufacturing techniques may be used to manufacture the lens or the lens series, and the technique used will typically depend on the type of lens to be manufactured as well as the types of surfaces that the lens or lenses are to have. For example, in the case of soft contact lenses, the manufacturing technique may use molds to manufacture the lens or lenses. Typically, many soft contact lenses are manufactured on a manufacturing line that uses processes, materials and equipment to make the lens and inspect the lens to ensure it is suitable for shipment to customers.

A different technique may be used to manufacture phakic IOC lenses. Likewise, a different technique may be used to manufacture hard contact lenses. In addition, the technique that is used to manufacture the lens or lenses may depend on the selected power profile. For example, the technique used to manufacture a soft contact lens having a continuous power profile defined mathematically by a polynomial may be different from the technique used to manufacture a soft contact lens having a discontinuous power profile defined mathematically by a piecewise function or spline. Persons skilled in the art will know how to select the appropriate manufacturing technique for the selected lens design.

It should be noted that the entity that selects the power profile for the peripheral portion may be, but need not be, the same entity that designs and manufactures of the lens. Likewise, the entity that manufactures the power profile for the peripheral portion may be, but need not be, the same entity that designs the lens. Thus, a single entity or three or more entities may perform the process represented by the flowchart illustrated in FIG. 5.

It should be noted that the invention has been described with reference to certain illustrative embodiments and that the invention is not limited to the embodiments described herein. For example, FIGS. 3 and 4 show certain power profiles that have been described herein for exemplary purposes, and the invention is not limited to these profiles. Persons skilled in the art will understand, in view of the disclosure provided herein, the manner in which other power profiles can be selected that provide the peripheral portion of the lens with a desired optical control.

What is claimed is:

1. A lens for controlling a location at which a peripheral vision image is focused relative to a retina of an eye, the lens comprising:
    a central portion having at least one optical zone that provides optical control over light rays passing through the central portion, the central portion having a power profile that optically controls a location at which a center vision image is focused relative to a retina of an eye, wherein the central portion extends a radial distance from a center of the lens outwardly toward a periphery of the central portion that is between about 3.5 millimeters (mm) and about 4.0 mm,
    a peripheral portion having at least one optical zone that provides optical control over light rays passing through the peripheral portion, the peripheral portion having a power profile that optically controls a location at which a peripheral vision image is focused relative to a retina of an eye, wherein the power profile of the peripheral portion is defined by a mathematical function that is discontinuous at the boundary where the periphery of the central portion meets the peripheral portion such that a first derivative of the function is not obtainable, and wherein the optical power provided by the power profile of the central portion at the boundary and the optical power provided by the power profile of the peripheral portion at the boundary differ by no more than about 8.0 Diopters; and
    wherein the lens, when worn on a person's eye, provides myopic defocus of the peripheral vision image that helps prevent or inhibit growth of the eye.

2. The lens of claim 1, wherein the optical power provided by the power profile of the central portion at the boundary and the optical power provided by the power profile of the peripheral portion at the boundary differ by no more than about 3.0 Diopters.

3. The lens of claim 1, wherein the mathematical function is a piecewise function.

4. The lens of claim 1, wherein the lens is a soft contact lens.

5. The lens of claim 1, wherein the lens is a hard contact lens.

6. The lens of claim 1, wherein the lens is a phakic intraocular (IOC) lens.

7. A lens for controlling a location at which a peripheral vision image is focused relative to a retina of an eye, the lens comprising:
    a central portion having at least one optical zone that provides optical control over light rays passing through the central portion, the central portion having a power profile that optically controls a location at which a center vision image is focused relative to a retina of an eye, wherein the central portion extends a radial distance from a center of the lens outwardly toward a periphery of the central portion that is between about 3.5 millimeters (mm) and about 4.0 mm
    a peripheral portion having at least one optical zone that provides optical control over light rays passing through the peripheral portion, the peripheral portion having a power profile that optically controls a location at which a peripheral vision image is focused relative to a retina of an eye, wherein the power profile of the peripheral portion is defined by a mathematical function that is continuous at the boundary where the periphery of the central portion meets the peripheral portion and that is not differentiable in a first derivative at the boundary, and wherein the optical power provided by the power profile of the central portion at the boundary and the optical power provided by the power profile of the peripheral portion at the boundary differ by no more than about 8.0 Diopters, and
    wherein the lens, when worn on a person's eye, provides myopic defocus of the peripheral vision image that helps prevent or inhibit growth of the eye.

8. The lens of claim 7, wherein the optical power provided by the power profile of the central portion at the boundary and the optical power provided by the power profile of the peripheral portion at the boundary differ by no more than about 3.0 Diopters.

9. The lens of claim 7, wherein the mathematical function is a spline.

10. The lens of claim 7, wherein the lens is a soft contact lens.

11. The lens of claim 7, wherein the lens is a hard contact lens.

12. The lens of claim 7, wherein the lens is a phakic intraocular (IOC) lens.

13. A method for providing a lens to be worn on a person's eye that prevents or inhibits myopia by preventing or inhibiting eye growth, the method comprising:
    selecting a power profile for a peripheral portion of a lens to be designed, the power profile of the peripheral portion optically controlling a location at which a peripheral vision image is focused relative to a retina of an eye, the lens having a central portion, the central portion having a power profile that optically controls a location at which a center vision image is focused relative to a retina of an eye, wherein the central portion extends a radial distance from a center of the lens outwardly toward a periphery of the central portion that is between about 3.5 millimeters (mm) and about 4.0 mm, and wherein the peripheral portion extends a radial distance from a boundary where the periphery of the central portion meets the peripheral portion to a periphery of the peripheral portion of about 3.5 mm to about 4.0 mm; and
    producing a design of a lens having the central portion and the peripheral portion, the peripheral portion having the selected power profile, wherein the power profile of the peripheral portion is defined by a mathematical function that is discontinuous at the boundary where the periphery of the central portion meets the peripheral portion such that a first derivative of the function is not obtainable, and wherein the optical power provided by the power profile of the central portion at the boundary and the optical power provided by the power profile of the peripheral portion at the boundary differ by no more than about 8.0 Diopters; and
    wherein the lens, when worn on a person's eye, provides myopic defocus of the peripheral vision image that helps prevent or inhibit growth of the eye.

14. The method of claim 13, further comprising:
    manufacturing a lens or a plurality of lenses having the lens design.

15. The method of claim 13, wherein the optical power provided by the power profile of the central portion at the boundary and the optical power provided by the power profile of the peripheral portion at the boundary differ by no more than about 3.0 Diopters.

\* \* \* \* \*